(12) United States Patent
Sheppard et al.

(10) Patent No.: US 7,749,727 B1
(45) Date of Patent: Jul. 6, 2010

(54) GENERATION OF ELECTROPOTENTIAL USING BACTERIAL CULTURE

(75) Inventors: John D. Sheppard, Cary, NC (US); Kartik Madiraju, Brossard (CA)

(73) Assignee: Triconic International Inc., Beaconfield, Quebec (CA)

( * ) Notice: Subject to any disclaimer, the term of this patent is extended or adjusted under 35 U.S.C. 154(b) by 272 days.

(21) Appl. No.: 11/777,715

(22) Filed: Jul. 13, 2007

(51) Int. Cl.
  *C12Q 1/02* (2006.01)
  *C12N 1/00* (2006.01)
  *C12N 1/12* (2006.01)
  *H01M 8/16* (2006.01)

(52) U.S. Cl. ............... 435/29; 435/243; 435/252.1; 429/2

(58) Field of Classification Search ............ None
  See application file for complete search history.

(56) References Cited

U.S. PATENT DOCUMENTS

| | | | |
|---|---|---|---|
| 4,385,119 | A | 5/1983 | Blakemore |
| 4,394,451 | A | 7/1983 | Blakemore et al. |
| 4,452,896 | A | 6/1984 | Blakemore et al. |
| 2006/0073540 | A1 * | 4/2006 | Martel ............ 435/34 |

OTHER PUBLICATIONS

Richard Blakemore, Magnetotactic Bacteria, article, Oct. 24, 1975, pp. 377-379, vol. 190, Woods Hole Oceanographic Institution, Woods Hole, Massachusetts.
The Regents of the University of California, *Magnetospirillum magnetotacticum*, Internet website www.genome.jgi-psf.org/draft_microbes/magma/magma.home.html, Copyright 2004, p. 1, The Regents of the University of California.
R.P. Blakemore, D. Maratea, and R.S. Wolfe, Journal of Bacteriology, Isolation and Pure Culture of a Freshwater *Magnetic spirillum* in Chemically Defined Medium, article, Copyright 1979, pp. 720-729, vol. 140, No. 2, Department of Microbiology, University of New Hampshire, Durham, New Hampshire 03824 and Department of Microbiology, University of Illinois, Urbana, Illinois 61801.
K.H. Schleifer, D. Schiller, S. Spring, M. Weiznegger, R. Amann, W. Ludwig and M. Kohler, System Appl. Microbiol., The genus *Magnetospirillum* gen. nov. description of *gryphiswaldense* sp. nov. and transfer of *Aquasprillum magnetotacticum* to *Magnetospirillum magnetotacticum* comb. nov., article, Copyright 1991, pp. 379-385, vol. 14, Gustav Fischer Verlag, Stuttgart/New York.
S. Seong and T.H. Park, Biotechnology and Bioengineering, Swimming Characteristics of Magnetic *Bacterium magnetospirillum* sp. AMB-1, and Implications as Toxicity Measurement, article, Copyright 2001, pp. 11-16, vol. 76, No. 1, John Wiley & Sons, Inc.
C-D Yang, H. Takeyama, T. Tanaka, and T. Matsunaga, Enzyme and Microbial Technology, Effects of growth medium composition, iron sources and atmospheric oxygen concentrations on production of luciferase-bacterial magnetic particle complex by a recombinant *Magnetospirillum magneticum* AMB-1, article, Copyright 2001, pp. 13-19, vol. 29, Elsevier Science, Inc.
D. Schuler, Int. Microbiol, The biomineralization of magnetosomes in *Magnetospirillum gryphiswaldense*, review article, Copyright 2002, pp. 209-214, vol. 5, Springer-Verlag and SEM.
D. Schultheiss, M. Kube, and D. Schiller, Applied and Environmental Microbiology, Inactivation of the Flagellin Gene flaA in *Magnetospirillum gryphiswaldense* Results in Nonmagnetotactic Mutants Lacking Flagellar Filaments, article, Copyright 2004, pp. 3624-3631, vol. 70, No. 6, American Society for Microbiology.
Y. Amemiya, T. Tanaka, B. Yoza, and T. Matsunaga, Journal of Biotechnology, Novel detection system for biomolecules using nanosized bacterial magnetic particles and magnetic force microscopy, article, Copyright 2005, pp. 308-314, vol. 120, Elsevier B.V.

* cited by examiner

*Primary Examiner*—Janet L Epps-Smith
(74) *Attorney, Agent, or Firm*—Smith Moore Leatherwood LLP

(57) ABSTRACT

A device is described for the generation of electropotential by bacterial culture that contain magnetic inclusions. As these bacteria move within an aqueous conductive environment, the generated magnetic fields induce a voltage between electrodes immersed in the solution. Current flow and power production can be sustained for several hours.

11 Claims, 7 Drawing Sheets

GENERATION OF ELECTROPOTENTIAL USING BACTERIAL CULTURE

BACKGROUND

This invention is directed generally to methods for generating electricity from bacterial culture.

Generation of power from non-traditional sources is a desirable goal. In recent decades, it has become increasingly necessary to find a non-toxic, efficient, renewable and cost-effective alternative energy resource. This is because non-renewable resources such as oil are being depleted at an alarming rate. The search for the ideal energy resource has led to the development of various power supplies including Aeolian, hydro, nuclear, and biomass. However, these resources, although renewable, are either inefficient (wind power), or potentially hazardous (nuclear energy).

Electricity can be produced through the principles of electromagnetism. For example, a horizontally spinning magnet suspended in a copper coil generates a magnetic field, aligning the atoms of the coil with common poles. Electrons in the copper coil atoms begin to flow through the coil, because of the polar gradient, inducing electric current.

In 1975, bacteria of the genus *Aquaspirillum* were found to have magnetic properties which they use to travel along the earth's magnetic field lines, towards lower oxygen concentrations. These unique properties were labeled as magnetotaxis. In 1979, Blakemore, D. Maratea and R. S. Wolfe collaborated to isolate and form a pure culture of a freshwater magnetic spirillum (strain MS-1) in a chemically defined growth medium.

In 1991 K. Schleifer et al. proposed a new genus species name for the magnetic spirilla bacteria. Magnetic bacteria are shown to respond to increased levels of toxic materials such as acetone and propanol. These bacteria respond by decreased motility and magnetic field strength. Yang et al., in 2001 discovered that enhancing the growth medium with peptone, yeast extract, L-cystine and more succinic acid decreased the lag phase before bacterial growth.

In 2002, D. Schiller studied the benefits of biomineralization of magnetosomes from gryphiswaldense. Biomineralization is the process by which a bacterium forms magnetite crystals enclosed in a membrane in its body. D. Schultheiss et al., (2004) found that inactivating the flagella of magnetic bacteria resulted in mutants that were not magnetotactic (magnetic, but cannot move along the magnetic field lines of the earth).

Another discovery concerning this bacterium was in 2005 (Amemiya et al.) who found that the magnetic particles in the bacteria can be used in immunoassays and in DNA detection systems.

SUMMARY OF THE INVENTION

The present invention is directed to, among other things, a device comprising bacterial culture, the movement of which in aqueous conductive solution generates an electrical potential. Furthermore, the present invention is directed to the use of bacterial culture and aqueous conductive solution contained within a device such as a reactor cell or generator. In another embodiment, the reactor cell or generator is connected to an electrical potential sensing device or power consuming device. In still a further embodiment of the present invention, the bacterial culture is comprised of strain MS-1. Other embodiments are described herein and set forth in the claims herein.

BRIEF DESCRIPTION OF THE FIGURES

The foregoing and other features, aspects, and advantages of the present invention will become better understood with regard to the following description, appended claims, and accompanying drawings where:

DEFINITIONS

Figure 1:
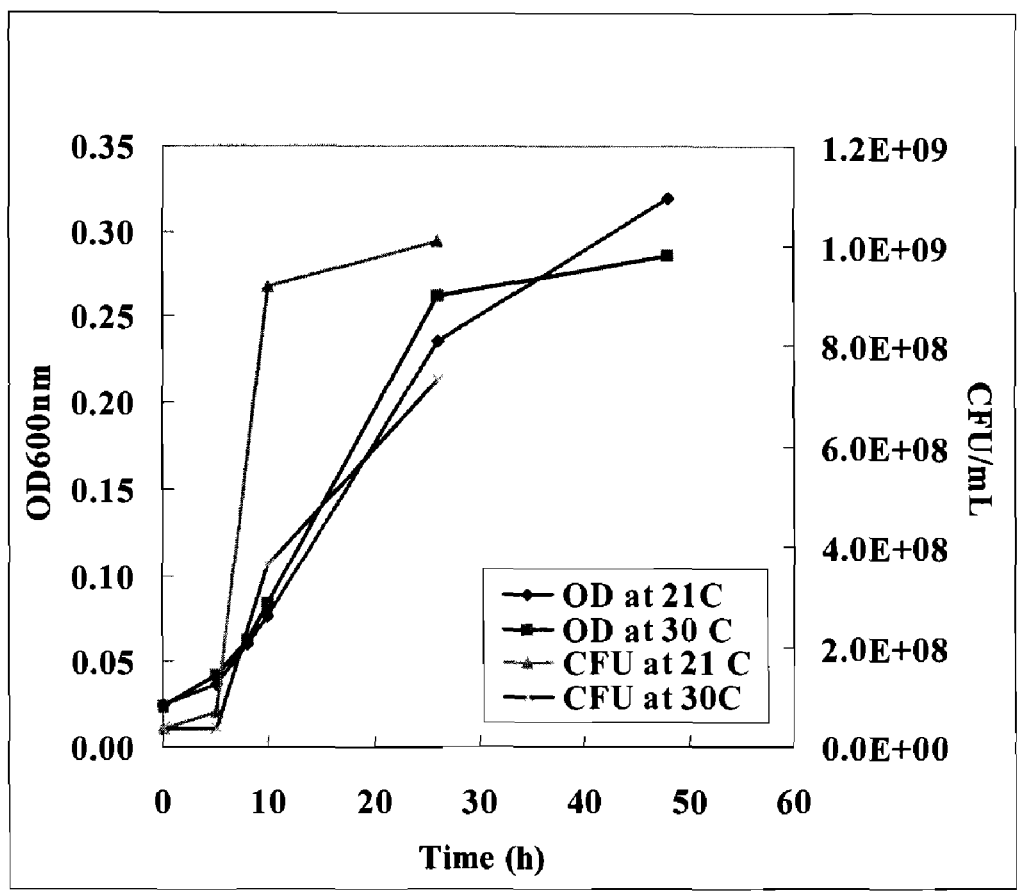
FIG. 1 is a graph showing the growth of MS-1 under specific conditions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "electrical potential" generally refers to the potential energy of a unit positive charge at a point in an electric field that is reckoned as the work which would be required to move the charge to its location in the electric field from an arbitrary point having zero potential.

The term "bacterial culture" generally refers to a population of living bacterial cells.

The term "MS-1" generally refers to a strain of motile magnetotactic bacteria belonging to the genus *Magnetospirillum* and available from the American Type Culture Collection (ATCC), Manassas Va., under number 700264.

The term "magnetic inclusions" generally refers to intracellular magnetic crystals formed by *Magnetospirillum* bacteria.

The term "reactor cell" generally refers to a physical device that contains the aqueous solution and bacterial culture in a configuration that allows a voltage to be produced and detected and could be used as a generator of electrical power.

These terms may be defined with additional language in the remaining portions of the specification.

DETAILED DESCRIPTION

The present invention is directed to, among other things, a device comprising bacterial culture, the movement of which in aqueous conductive solution generates an electrical potential. Furthermore, the present invention is directed to the use of bacterial culture and aqueous conductive solution contained within a device such as a reactor cell or generator. In another embodiment, the reactor cell or generator is connected to an electrical potential sensing device or power consuming device. In still a further embodiment of the present invention, the bacterial culture is comprised of strain of motile magnetotactic bacteria, *Magnetospirillum* MS-1, generally referred to herein as MS-1. Other embodiments are described herein and set forth in the claims herein.

It has been found that one aspect of bacterial culture including magnetic properties is the generation of power as set forth herein. In an aspect, the various devices provided herein are useful for generation of electricity using *Magnetospirillum* bacteria by providing the means of converting the metabolic activity and movement of the bacterial cells by containing this activity within an aqueous conductive solution in which two electrodes have been placed. Further this invention enables the determination of the optimum concentration of bacteria that yields high, sustainable voltages. It also allows the device to be used for testing the effectiveness of electricity production with strain MS-1 versus its non-magnetic mutant, to demonstrate the necessity for magnetic properties.

The present invention also allows a method to be devised to measure efficiency of energy conversion from substrate to electricity, and experimenting with ways to enhance the efficiency.

It should be apparent to one skilled in the art that various embodiments and modifications may be made to the invention disclosed in this application without departing from the scope and spirit of the invention. Various publications mentioned herein are cited for the purpose of describing and disclosing reagents, methodologies and concepts that may be used in connection with the present invention.

Electromechanical theory describes how the interaction between magnetic and electrical fields results in the production of a mechanical force. Likewise, if a mechanical force is applied to move a conductor through a stationary magnetic field, then an electrical field or potential is generated in the conductor. In the case of the present invention, a moving magnetic field(s) is produced by a culture of motile magnetotactic bacteria, *Magnetospirillum* MS-1, which are contained within a conducting aqueous solution inside a reactor cell or generator, in this case of about 1 cm×1 cm×4.5 cm deep. The movement of these microbial magnets within the conducting fluid, which spontaneously align due to the effect of the earth's magnetic field, generate an electrical potential that can be measured by placing two electrodes on parallel walls of the generator.

The interaction of the individual magnetic fields is not simply additive, as there is a minimum and maximum cell density that is the most effective in sustaining the electrical potential. If there is no appreciable current flow, as occurs when there is a very large resistance between the electrodes (for example several million ohms as would be encountered from the connection of a voltmeter), then there is no counter magnetomotive force that would tend to stop the motion of the bacteria. Under these conditions there is, therefore, no actual energy conversion between the metabolism of the bacteria and the electrical circuit. However, if the voltmeter is replaced with a smaller resistance, such as 10,000 ohms, there is an appreciable current developed that generates its own magnetic field in opposition to that produced by the motion of the magnetic bacteria.

The continued motion of the bacteria requires an expense of metabolic energy which is then transferred to the electrical circuit as electrical power. Thus, the microbial generator, as described, is an effective means of transforming chemical energy originating from the nutrient sources of the bacteria into a usable form of electrical energy. It is fully anticipated that the device can be configured and scaled-up as individual cells connected together in various combinations of series and parallel circuits to achieve whatever performance characteristics are desired. As long as the bacteria are able to maintain their viability and associated movement within the conducting environment, the electrical potential should be maintained. Thus, design of the reactor cell as a continuous or semi-continuous system in which there are regular additions of the appropriate nutrients to maintain viability of the culture could maintain the electrical power output indefinitely.

Figure 5:
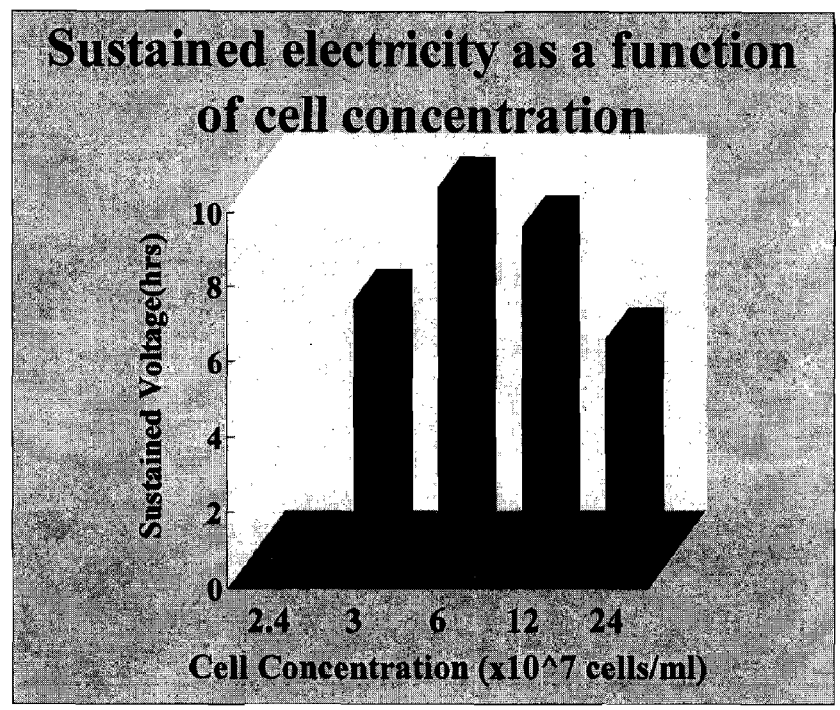
FIG. 5 is a graph showing the number of hours for which voltage is sustained as a function of cell concentration.

The first step in making a device as set forth herein was to grow the bacterial culture to sufficient cell density (FIG. 1), using an enhanced growth medium. The next step was to configure the device as a reactor cell or generator incorporating electrodes, so as to have the means of quantifying voltage and power production (FIGS. 2*a*-2*c*) from the bacterial culture. Once these configurations were constructed, various data were collected to demonstrate how voltage could be sustained for extended periods of time, generally in excess of 20 hours and often for as long as 48 hours depending on the conditions of the test. The importance of cell density was found and, as illustrated in FIG. 5, a concentration of from about 6 to about $12 \times 10^7$ per mL gave the most sustainable voltage under the conditions tested.

Figure 6:
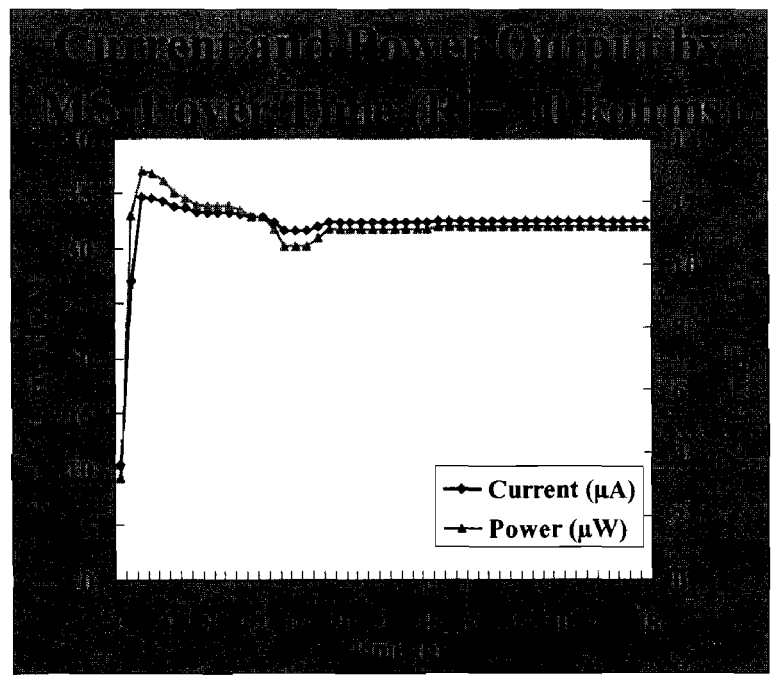
FIG. 6 is a graph showing 3-trial average of current and power output by MS-1 over 48 hours.
Figure 7:
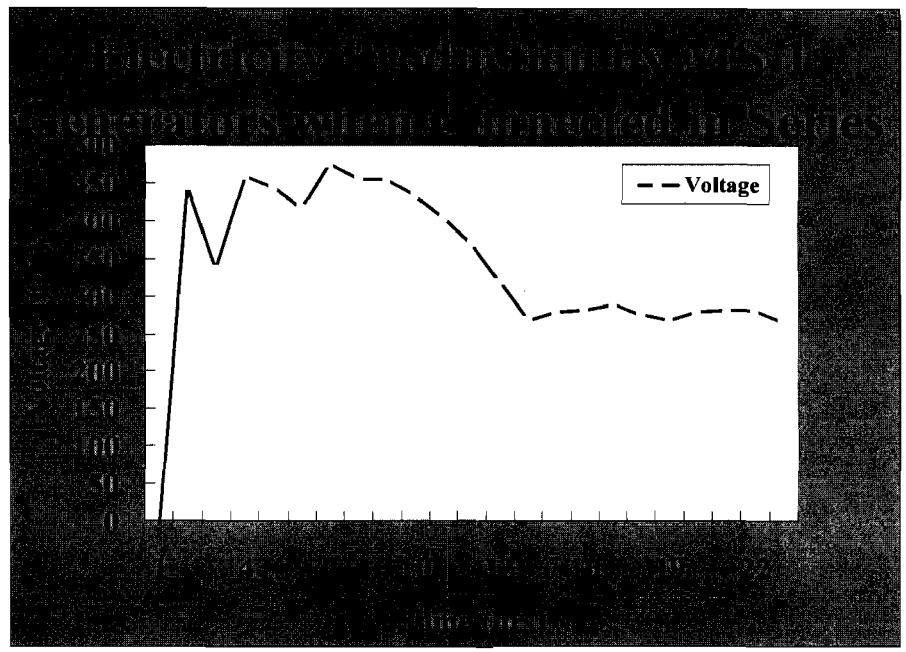
FIG. 7 is a graph showing voltage generated from two MS-1 generators connected in series.
Figure 8:
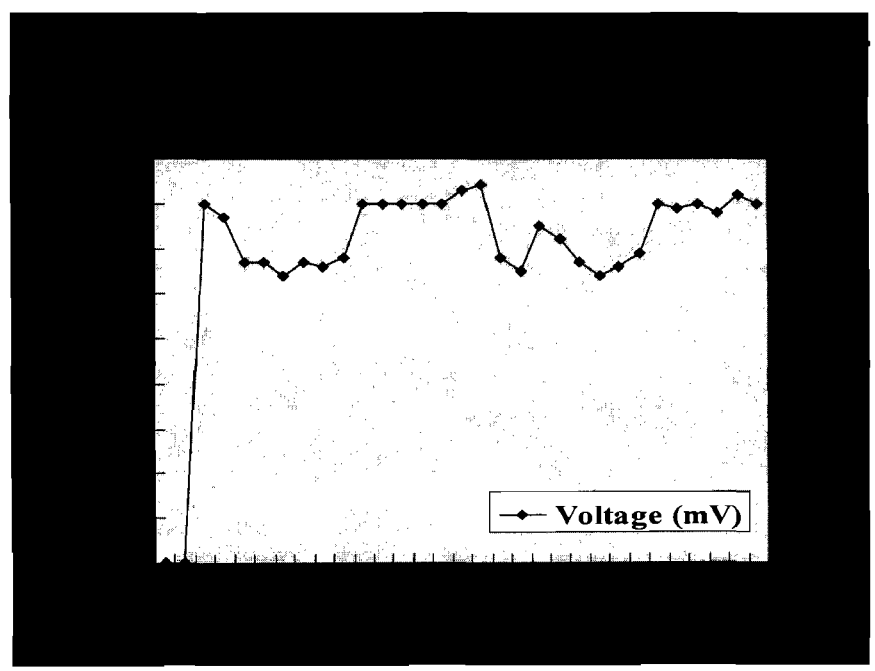
FIG. 8 is a graph showing electricity production by four generators connected in series.

To demonstrate that the reactor cells or generators could also sustain current and, therefore produce power, a 10,000 ohm load resistor was placed across the electrodes. FIG. 6 shows how 11 microwatts of power was sustained for 48 hours of continuous operation from a single reactor cell. It was also shown how the reactor cells could be configured in either series or parallel configurations. As would be expected from electrical theory, four reactor cells in series produced about twice the voltage as from two (FIGS. 7 and 8). Connecting the generators in parallel did not result in an elevated voltage (FIG. 9) but could produce higher current and more power than a single cell.

Figure 10:
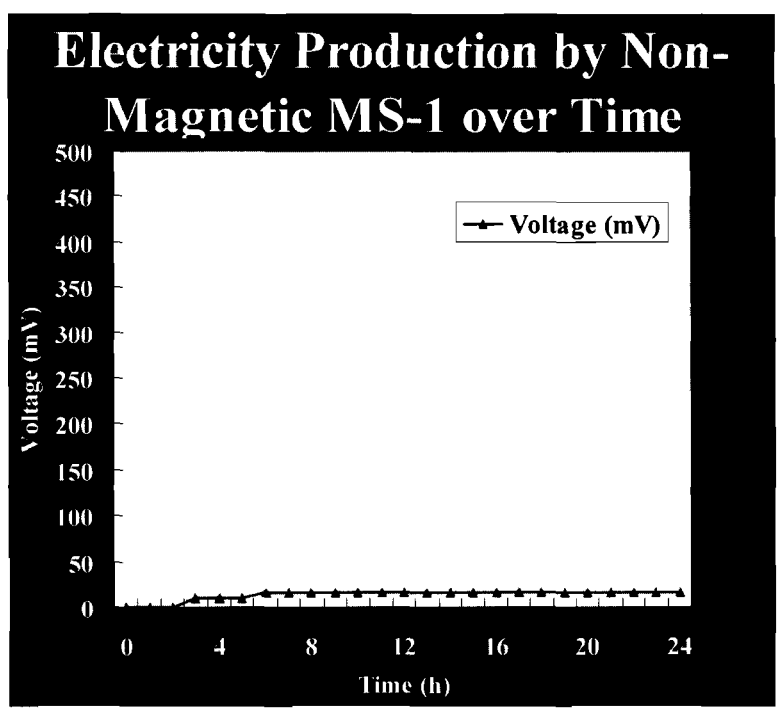
FIG. 10 is a graph showing voltage production by non-magnetic MS-1, cultured in iron deficient medium.

A culture of *Magnetospirillum* was also grown in the absence of a source of iron to prevent the formation of the magnetite crystals. FIG. 10 confirms that the magnetic properties of these bacteria are required for the generation of electricity.

EXAMPLES

The following examples are provided to illustrate the invention and do not limit the scope of the claims.

Example 1

*Magnetospirillum* sp., designated here as MS-1, available from the American Type Culture Collection, Manassas Va., as number ATCC 700264, is cultured using the enhanced growth medium (the composition of which is contained in Table 1) in an unshaken flask incubated at a temperature of 30° C.

TABLE 1

Enhanced Growth Medium MS-1
MSGM (magnetospirillum growth medium)

| Regular | Enhanced | Ingredient |
|---|---|---|
| | In 1 L of dH$_2$O | |
| Add | | |
| 5 | 5 | mL Wolfe's Mineral Solution |
| 2 | 2 | mL 0.01 M ferric quinate (see below for recipe) |
| 450 | 450 | uL 0.1% resazurin |
| 0.68 | 0.68 | g KH$_2$PO$_4$ |
| 0.12 | 0.12 | g NaNO$_3$ |
| 0.035 | 0.035 | g L-Ascorbic acid |
| 0.37 | 0.37 | g Tartaric acid |
| 0.39 | 11.1 | g succinic acid (full dissolution after autoclaving) |
| 0.05 | 0.05 | g sodium acetate |
| | 0.2 | g polypeptone |
| | 0.1 | g yeast extract |
| | 0.05 | g L-cysteine |
| Adjust pH to 6.7 with 1 M NaOH | | |
| Autoclave for more than 30 min | | |
| After autoclaving, add | | |
| 10 | 10 | mL Wolfe's Vitamin Solution |
| 0.01 M Ferric Quinate | Add into 100 mL dH$_2$O | 0.27 g FeCl$_3$ 0.19 g Quinic Acid |

Figure 2A:
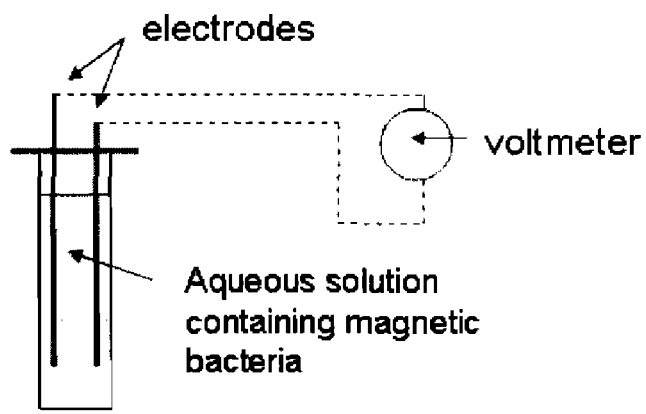
FIG. 2a is a cross-sectional side view of a single reactor cell apparatus to demonstrate bacteria generating electrical potential.
Figure 3:
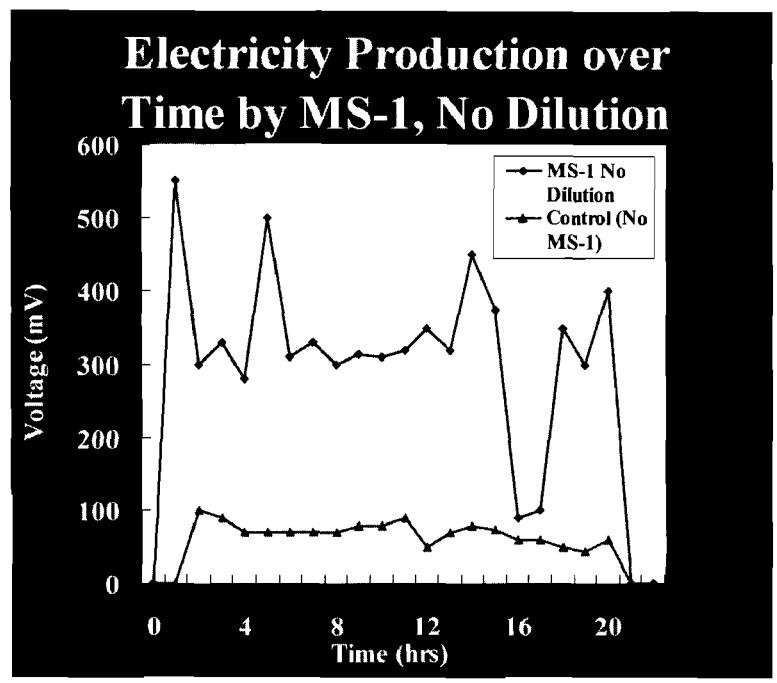
FIG. 3 is a graph showing voltage produced by an undiluted culture of MS-1 for over 20 hours.

As shown in FIG. 1, the growth of the culture is typically completed within 20 hours, after which approximately 2 mL of the culture is transferred to a reactor cell without dilution. Two aluminum electrodes are inserted on opposite sides of the reactor cell, immersed in the solution containing the active bacterial culture. Referring to the diagram of FIG. 2a, a wire is firmly attached to each electrode and then connected to a high impedance voltmeter, such as an ABB Goerz Model SE 420, which also has the facility to provide a real-time chart record of the voltage over time. The reactor cell is maintained at room temperature and the voltage output monitored for the next 48 hours. As an experimental control, the voltage output from an additional reactor cell is monitored in the absence of the bacterial culture. Typical results are illustrated in FIG. 3.

Example 2

Figure 4:
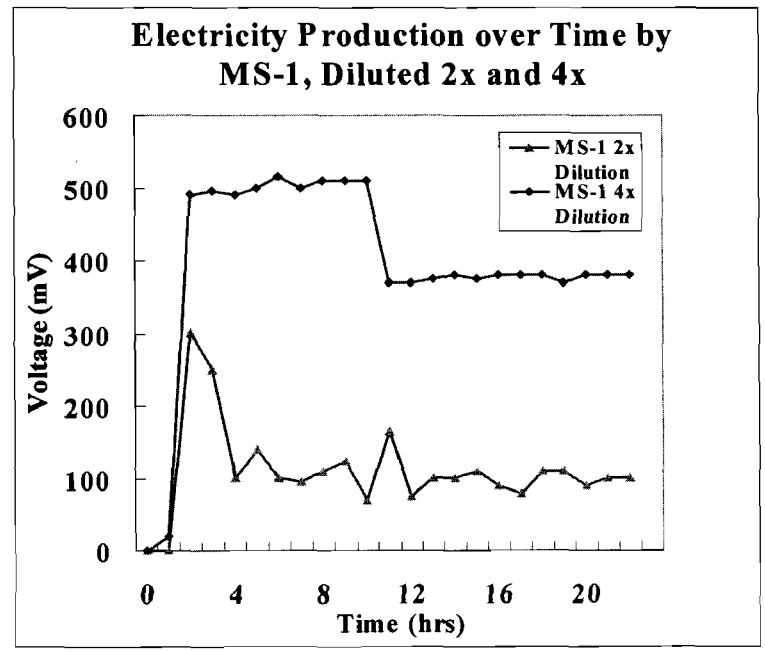
FIG. 4 is a graph showing voltage produced by a culture of MS-1 at two different dilutions.

The same procedure for growth of the *Magnetospirillum* sp. is followed as described in Example 1. However, in this example, the culture is introduced into the reactor cell and diluted with an appropriate volume of salt solution to obtain different cell concentrations. The production of electrical potential at two different dilutions of the bacterial culture is shown in FIG. 4, while FIG. 5 shows how the cell concentration also affects the duration of the voltage production.

Example 3

Figure 2B:
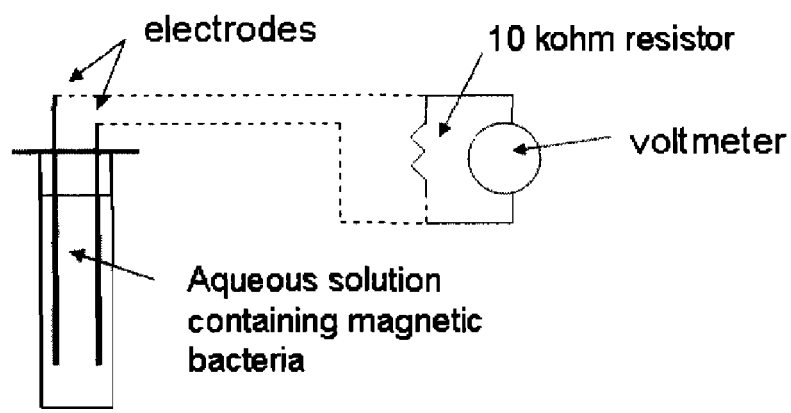
FIG. 2b is a cross-sectional side view of two reactor cells connected in series apparatus to demonstrate bacteria generating electrical potential.

The same procedure for growth of the *Magnetospirillum* sp. is followed as described in Example 1. The culture is placed in a reactor cell with an appropriate dilution, ideally to obtain from about 3 to about 12×10$^7$ cells per mL. The electrodes are inserted and wires attached, however, the electric circuit is modified from previous examples by placing a 10,000 ohm resistor between the two wires attached to the electrodes. The voltmeter is then connected across the resistor as shown in FIG. 2b. This circuit has a reduced resistance and allows for the current that flows between the electrodes to be quantified by the measurement of voltage drop across the 10 kohm resistor. The product of the current and voltage drop is the power produced by the reactor cell. The results from such an experiment are shown in FIG. 6.

Example 4

Figure 2C:
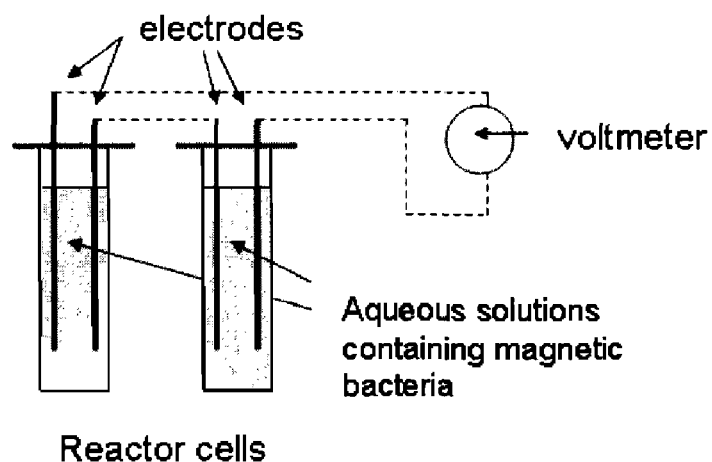
FIG. 2c is a cross-sectional side view of two reactor cells connected in parallel apparatus to demonstrate bacteria generating electrical potential.

The same procedure for growth of the *Magnetospirillum* sp. is followed as described in Example 1. The culture is placed in a reactor cell with an appropriate dilution, ideally to obtain from about 3 to about 12×10$^7$ cells per mL. The electrodes are inserted and wires attached, however, the electric circuit is modified from previous examples by connecting two or more reactor cells in a series electrical configuration as shown in FIG. 2c. The voltage produced from series configurations of both two and four reactor cells are shown in FIGS. 7 and 8 respectively.

Example 5

Figure 2D:
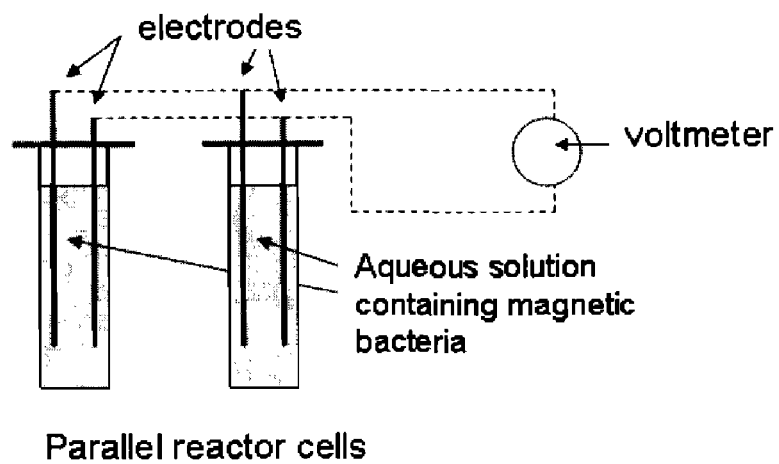
FIG. 2d is a cross-sectional side view of connecting two reactor cells in a parallel electrical configuration as shown in FIG. 2d.

The same procedure for growth of the *Magnetospirillum* sp. is followed as described in Example 1. The culture is placed in a reactor cell with an appropriate dilution, ideally to obtain between 3-12×10$^7$ cells per mL. The electrodes are inserted and wires attached, however, the electric circuit is modified from previous examples by connecting two reactor cells in a parallel electrical configuration as shown in FIG. 2d. The voltage produced from the parallel configuration is presented in FIG. 9.

Example 6

The same procedure for growth of the *Magnetospirillum* sp. is followed as described in Example 1 except that the medium lacks the ferric quinate which serves as a source of iron for the production of the magnetic properties of the bacteria. The culture is placed in a reactor cell with an appropriate dilution, ideally to obtain between 3-12×10$^7$ cells per mL. The electrodes are inserted and wires attached as shown in FIG. 2a. The voltage is monitored but, as shown in FIG. 10, no appreciable voltage can be detected, demonstrating the need for the magnetic properties of the bacteria for the generation of electricity.

FIG. 1 shows a graph of the growth of MS-1 over time at two different temperatures to sufficient cell density. The lag phase is less than about 5 h, and the lag phase of growth is completed within 20 h. The maximum Optical Density at 600 nm was 0.33, while the maximum cell density achieved was 1.1×10$^9$ cells/ml.

FIG. 2a shows a diagram of the apparatus used to demonstrate the capability of the bacteria for generating an electrical potential from a single reactor cell.

FIG. 2b. shows a diagram of the apparatus used to demonstrate the capability of the bacteria for generating power from a single reactor cell.

FIG. 2c. shows a diagram of the apparatus used to demonstrate the capability of bacteria for generating an electrical potential when two reactor cells are connected in a series configuration.

FIG. 2d. shows a diagram of the apparatus used to demonstrate the capability of bacteria for generating an electrical potential when two reactor cells are connected in a parallel configuration.

FIG. 3 is a graph that shows the voltage produced by an undiluted culture of MS-1 for over 20 consecutive hours. Control generator (no bacteria) shows some noise, but remained below 100 mV. Use of concentrated MS-1 inoculation might be the reason for the voltage instability.

FIG. 4 is a graph that shows the electricity produced by MS-1 after 2× and 4× dilution, over about 20 hrs. At a 2× dilution, voltage is sustainable for 9 hrs, at about 100 mV. However, voltage remained below 200 mV for most of the experimental duration. At a 4× dilution, voltage was sustained for about 8 hrs at about 500 mV, and then dropped to about 375 mV for about 10 hrs.

FIG. 5 is a graph that shows the number of hours for which voltage is sustained, as affected by cell concentration in the generator. These results show that the optimum sustainability can be achieved using from about 6 to about $12\times10^7$ cells per mL.

FIG. 6 is a graph that shows the 3 trial average of current and power output by MS-1 over 48 hrs with an applied resistance of 10 kilo ohms. Power is sustainable beyond 48 h at about 11 microwatts, and current is sustainable beyond 48 h at about 33 microamps.

FIG. 7 is a graph that shows the voltage generated from two MS-1 generators connected in series as monitored over 20 h. The voltage was relatively sustainable throughout the experiment, remaining above 300 mV.

FIG. 8 is a graph that shows electricity production by four generators connected in series over a 30 h period. Voltage is relatively sustainable throughout the experiment, from about 700 to about 800 mV, approximately twice what was achieved from 2 reactors in series (FIG. 7).

Figure 9:
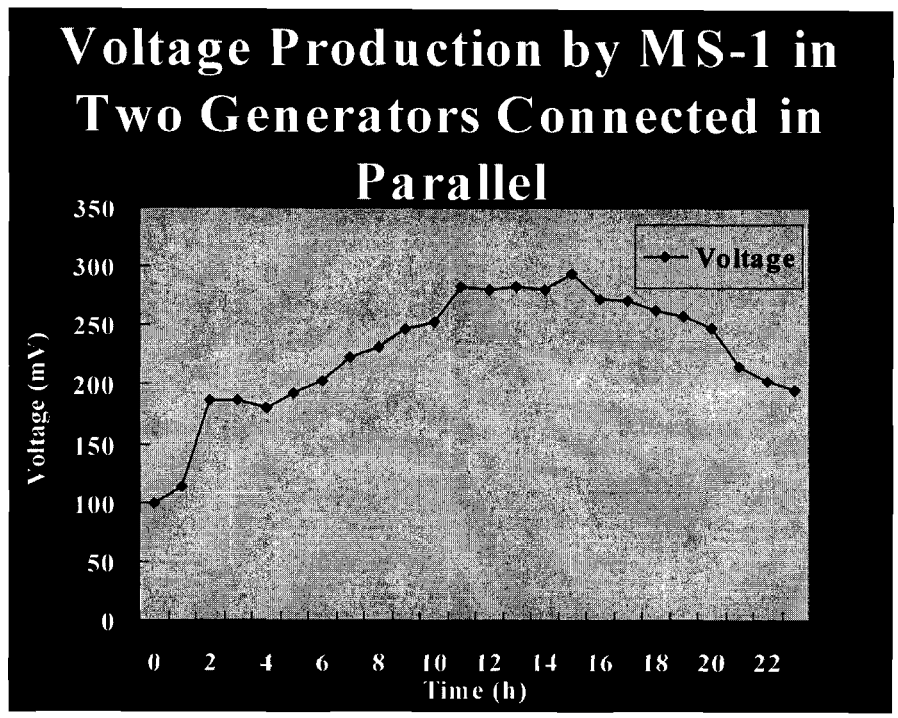
FIG. 9 is a graph showing voltage production by MS-1 from two generators connected in parallel.

FIG. 9 is a graph that shows the voltage production (average of 3 trials) by MS-1 from two generators connected in parallel, over a 22 h period. Voltage increased to 250 mV after 7 h, and remained sustainable between 250-300 mV for about 10 h, before decreasing steadily to 200 mV.

FIG. 10 is a graph that shows the electricity produced (average of 3 trials) by non-magnetic MS-1, over about 24 hrs. Voltage is insignificant, sustained at 15 mV for the duration of the experiment. In typical control experiments (no bacteria), voltage is less than 100 mV, mostly from random noise. FIG. 10 confirms that the magnetic properties of these bacteria are required for the generation of electricity.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

What is claimed is:

1. A microbial generator device comprising:
   a bacterial culture comprising a species from the genus *Magnetospirillum*, the movement of which in aqueous conductive solution generates an electrical potential;
   a reactor cell or generator in which said bacterial culture and said aqueous conductive solution are contained; and
   two electrodes;
   wherein said electrodes are in communication with said reactor cell or generator and in communication with an electrical potential sensing device or power consuming device; and
   wherein electrical potential (voltage) is produced by the microbial generator device.

2. The microbial generator device of claim 1 in which the bacterial culture is comprised of *Magnetospirillum* sp. strain MS-1, AMB-1 or MSR-1.

3. The microbial generator device of claim 1 in which the bacterial culture is comprised of *Magnetospirillum magneticum*.

4. The microbial generator device of claim 1 in which the bacterial culture is comprised of *Magnetospirillum gryphiswaldense*.

5. The microbial generator device of claim 1 in which the bacterial culture is comprised of *Magnetospirillum magnetotacticum*.

6. The microbial generator device of claim 1, wherein the bacterial culture is grown in more than one reactor cell or generator connected in series.

7. The microbial generator device of claim 1, wherein the bacterial culture is grown in more than one reactor cell or generator connected in parallel.

8. The microbial generator device of claim 1, wherein the sensing device is a voltmeter that measures the production of electrical potential.

9. The microbial generator device of claim 1, wherein the said actual current is supplied to an external load to produce power.

10. The microbial generator device of claim 1, wherein the bacterial culture comprises at least $3\times10^7$ cells/mL.

11. The microbial generator device of claim 1, wherein a nutrient solution is added to said reactor cell or generator either semi-continuously or continuously.

\* \* \* \* \*